US012602787B2

(12) United States Patent (10) Patent No.: US 12,602,787 B2
Siré Langa et al. (45) Date of Patent: Apr. 14, 2026

(54) PROCEDURE FOR CONTROL, PROGNOSIS AND COMPARATIVE SUPPORT RELATED TO DERMATOLOGICAL LESIONS

(71) Applicant: SKILLED SKIN SL, Barcelona (ES)

(72) Inventors: Alberto Siré Langa, Saint Just Desvern (ES); David Reifs Jiménez, Barcelona (ES); Ibon Uribe Elorrieta, Galdakao (ES)

(73) Assignee: SKILLED SKIN SL, Barcelona (ES)

( * ) Notice: Subject to any disclaimer, the term of this patent is extended or adjusted under 35 U.S.C. 154(b) by 274 days.

(21) Appl. No.: 18/370,559

(22) Filed: Sep. 20, 2023

(65) Prior Publication Data

US 2024/0212151 A1     Jun. 27, 2024

(30) Foreign Application Priority Data

Dec. 21, 2022    (ES) ............................... ES202231088

(51) Int. Cl.
| | |
|---|---|
| *G06K 9/00* | (2022.01) |
| *A61B 5/00* | (2006.01) |
| *A61B 5/103* | (2006.01) |
| *G06T 7/00* | (2017.01) |
| *G06T 7/11* | (2017.01) |
| *G06T 7/62* | (2017.01) |
| *G06T 11/00* | (2006.01) |

(Continued)

(52) U.S. Cl.
CPC .......... *G06T 7/0014* (2013.01); *A61B 5/1032* (2013.01); *A61B 5/445* (2013.01); *G06T 7/11* (2017.01); *G06T 7/62* (2017.01); *G06T 11/001* (2013.01); *G06T 11/206* (2013.01); *G06V 10/25* (2022.01); *G06V 10/764* (2022.01); *G06V 10/82* (2022.01); *G06T 2207/20084* (2013.01); *G06T 2207/30088* (2013.01); *G06T 2207/30096* (2013.01); *G06V 2201/03* (2022.01)

(58) Field of Classification Search
CPC .................. A61B 5/1032; A61B 5/445; G06T 2207/30088; G06T 2207/20084; G06T 7/0012; G06V 10/82
See application file for complete search history.

(56) References Cited

U.S. PATENT DOCUMENTS

| | | | |
|---|---|---|---|
| 2016/0038092 A1* | 2/2016 | Golay ..................... | A61C 8/00 |
| | | | 600/408 |
| 2016/0206205 A1* | 7/2016 | Wu ........................ | A61B 5/445 |

(Continued)

OTHER PUBLICATIONS

Cazzolato, Mirela Teixeira, et al. "A DBMS-Based framework for content-based retrieval and analysis of skin ulcer images in medical practice." Proceedings. 2019. (Year: 2019).*

*Primary Examiner* — Hadi Akhavannik

(74) *Attorney, Agent, or Firm* — Schmeiser, Olsen & Watts, LLP

(57) ABSTRACT

An ulcer-related control, prognosis and comparative support procedure is provided that includes the following stages: measuring the area of the ulcer and ROI (1) by taking an image of the area of the ulcer and ROI (1.*a*), segmenting the tissues obtained in the image of the ulcer area and ROI (1.*a*)., obtaining the base characteristics vector, depicting the state of the tissues, classifying ulcers, supporting user's decisions, archiving registered clinical cases, and supporting user's decisions by comparing the global characteristics vector with the global characteristics vectors of the registered ulcer clinical cases.

4 Claims, 9 Drawing Sheets

(51) Int. Cl.
   G06T 11/20 (2006.01)
   G06V 10/25 (2022.01)
   G06V 10/764 (2022.01)
   G06V 10/82 (2022.01)

(56)     References Cited

U.S. PATENT DOCUMENTS

2019/0172197 A1\*  6/2019  Buckler ................. G06F 18/24
2019/0188851 A1\*  6/2019  Zouridakis ........... G06T 7/0012

\* cited by examiner

SUPPORTING DECISIONS

Tissue segmentation (2)

Evolution of the size of the ROI area (dermatological lesion)

Evolution of the dermatological lesion according to values of the characteristics of the reference scale (Resvech in the example) (6.c)

Wound size

PROCEDURE FOR CONTROL, PROGNOSIS AND COMPARATIVE SUPPORT RELATED TO DERMATOLOGICAL LESIONS

CROSS-REFERENCE TO RELATED APPLICATIONS

This application claims priority to ES Application No. P202231088, having a filing date of Dec. 21, 2022, the entire contents of which are hereby incorporated by reference.

FIELD OF TECHNOLOGY

This following relates to an ulcer-related control, prognosis and comparative support procedure, based on various imaging modalities and clinical and social parameters of the patient. Further, it is related to ulcers visible from the outside, such as skin ulcers.

BACKGROUND

A skin ulcer is a skin lesion that involves the loss of the epidermis, part of the dermis, and even the hypodermis; it can be a merely superficial wound or a deeper affectation. Among other causes of this condition, ulcers caused by diabetes, which can develop in 20% of patients, fall within the scope of embodiments of the invention. This is due to the affectation of the diabetic disease on vessels and nerves, fundamentally. On the other hand, they are patients who, due to their own underlying pathology, have a high risk of infection, causing significant complications. For this reason, it is extremely important to identify the ulcer's phase and apply the most appropriate treatment according to the needs of the patient, thereby avoiding unwanted complications. For this purpose, embodiments of the invention procedure for control, prognosis and support was developed, which is applicable to any type of (long-lasting) chronic ulcer.

SUMMARY

Traditionally, for the evaluation of ulcers, the wound area is evaluated by methods that require contact therewith, with the consequent disruption to the patient. Non-invasive methods for ulcer analysis are currently known, including those based on ulcer imaging.

As a reference to the state of the art, imaging-assisted ulcer analysis methods are known which determine the region of interest (ROI) of an ulcer, determine the wound boundary and calculate the area value in pixels, they segment the image and classify the ulcer tissues and assess ulcer healing based on reduction in ulcer area. But the support they offer to the professional is limited given that the images of ulcers and data that are compared with each other are always from the same wound in different phases and its evolution cannot be predicted in comparison with previous similar cases, nor do they assign a risk to each patient, not relating to relevant precedents to give adequate and effective support to the professional.

There are also methods to assess the risk of the patient based on the reduction of the wound area, although they do not carry out a classification of the tissues, based solely on the reduction of the total area of the ulcer and do not provide any support to the professional in decision-making or in determining the best treatment to follow.

Among the methods based on image taking, there are those that capture images at different wavelengths or using ultrasound, among others. But for this purpose, specific associated instruments are always required, not always within the reach of all users or health centers.

Faced with this state of the conventional art, embodiments of the present invention refer to an ulcer-related control, prognosis and comparative support procedure, which comprises the following stages:

Measuring the area of the ulcer and ROI (1) by capturing an image of the area of the ulcer and ROI (1.*a*).

Segmenting the tissues (2) obtained in the image of the ulcer area and ROI (1.*a*).

Obtaining the base characteristics vector (5)

Representing the analyzed data; state of the tissues (necrotic, slough . . . ) and surface area of the ulcer (in square centimeters).

Classifying ulcers.

Supporting decisions.

Archiving registered clinical cases.

In this patent, a vector or matrix is understood as a contiguous storage area that contains a series of elements of the same type, in our case, data. From the logical point of view, a matrix can be seen as a set of elements arranged in rows and columns, a vector being the set of elements of the matrix relating to a single row. The difference between vector and matrix lies in how these structures are accessed; while vectors are accessed with a subscript, matrices use two subscripts (they indicate the position in the row and column).

In embodiments of the present invention, the support for the user's decision is based on the comparison of vectors; in particular, the global characteristics vector (3) and the global characteristics vectors of the registered clinical cases (4). In the global characteristics vector (3), the global data that characterizes the ulcer-related clinical case that is being analyzed is stored and it is compared with the global characteristics vectors of the previous registered clinical cases of ulcers (4), these being the previously analyzed, stored, and recorded global characteristics vector set of ulcer clinical cases. Thanks to the comparison between vectors, case data can be compared in a structured and objective way, thus making it possible to locate the case or cases whose characteristics are closest to the characteristics of the ulcer being analyzed.

The patient's data vector (6) (a vector that includes the relevant data of the patient and accompany the specific clinical case for a better interpretation of the evolution of the ulcer area) is added to the base characteristics vector (5) obtained from the segmentation of the tissues (2) of the image of the area of the ulcer (1.*a*) (vector that includes the data of the area of the ulcer and the type of tissues that it comprises), in order to obtain a global characteristics vector (3) and this is compared with the global characteristics vectors of the registered clinical cases of ulcers (4) to obtain the registered clinical case whose characteristics are closest to the characteristics of the analyzed clinical case. This comparison is made by calculating the Euclidean distance (the mathematical equation that provides a numerical value representing the shortest distance between two vectors) between global characteristics vectors. This data will give us the global characteristics vector of the registered clinical cases (4) that is closest to the global characteristics vector (3) (the one whose Euclidean distance is the smallest), thus being the registered clinical case that most resembles the clinical case being analyzed. This procedure provides the user with data on the treatment used in the most similar registered ulcer clinical case and once obtained, the user will have access to the results of this treatment to assist in decision-making in a current real case with more information and accuracy.

The data vector of the patient (6) is obtained from the previously stored patient-related characteristics (6.*a*) (such as weight, height, age, etc.), the patient's clinical data (6.*b*) (such as clinical analyses (diabetes, anemia . . . ), clinical tests (thermography, ultrasound . . . ), medical history (previous injuries . . . ), etc.) and patient risk scale (6.*c*) (data from the scale indicated for each center, to assess each patient's ulcer-related risk, for example, Resvech). By introducing these data, the base vector obtained from tissue segmentation is improved, introducing values in the comparison such as risk factors such as diabetes, heart problems, etc., obtaining a much more complete global characteristics vector. The introduction in the vector of the risk-related data determined by the health center ensures that the results will be obtained based on a scale with which the user is familiar—the scale applied by the center to which he/she belongs. This makes it possible to standardize the use of the scale determined by the center, which is generally clinically validated, reducing subjectivity in the evaluation of ulcers by health staff.

The segmentation of the tissues (2) obtained in the image of the ulcer area and ROI (1.*a*) is performed using the pretrained CNN (Convolutional Neural Networks) that classifies the tissues as granulated, sloughy, and necrotic. In addition, since it is analyzed by the same CNN algorithm, the analysis of the tissues is not subject to different subjective interpretations by users, thus making it possible to compare the different cases that effectively determine the classification of the tissue.

The depiction of the tissues reconstructs the vector-based image of base characteristics (5) representing each type of tissue with a specific color (usually red for granules, yellow for slough and black for necrotic), which facilitates the interpretation of the ulcer by highlighting each tissue using colors on the image captured. This makes it easier for the user and specialist to check the evolution of the ulcer visually and quickly.

The measurement of the area of the ulcer and ROI (1) by imaging is carried out with the image taken of the region of interest (ROI) processed through an API (Application Programming Interface, which provides the distance in cm between two points on the image as a reference to use to calculate the area of the ROI), determining the ulcer area in cm². The image may be a conventional image, or a thermographic image. By this measurement, the user obtains the numerical value of the area in a recognized metric system without the need for the use of invasive methods requiring direct contact with the ulcer and the consequent disorders that the patient may present, or the complicated conversion of the area size provided to be able to interpret the progress of the ulcer. An added advantage is that since the procedure is based on an image that can be acquired with any mobile device such as a phone or tablet, patients do not have to travel from their usual homes. Therefore, it can be applied both in home care and in telecare. In addition, not only is the area of the ulcer analyzed, but also that of the ROI, which allows the surrounding area and its evolution to be observed over time, since the surrounding tissue may be affected. In some situations, this API can also be replaced by a biocompatible adhesive caliper that would be placed at the same level as the wound, always applied without direct contact with the ulcer.

In addition, this procedure ensures that the global characteristics vector (3) of the ulcer clinical case is archived in a secure environment. The global characteristics vector will become part of the global characteristics vectors of registered clinical cases (4) to be used as a reference in future clinical cases. Thus, the procedure will feed back, generating more and more clinical cases for comparison. In addition, integration with the storage system of the organization where it is implemented is allowed through different types of standards (HL7-FHIR, SAP, REST API, ad hoc . . . ). Since the global characteristics vector (3) contains patient data, the importance of adapting to clinical standards recognized by each health center is evident.

BRIEF DESCRIPTION

Some of the embodiments will be described in detail, with references to the following Figures, wherein like designations denote like members, wherein.

Figure 4A:
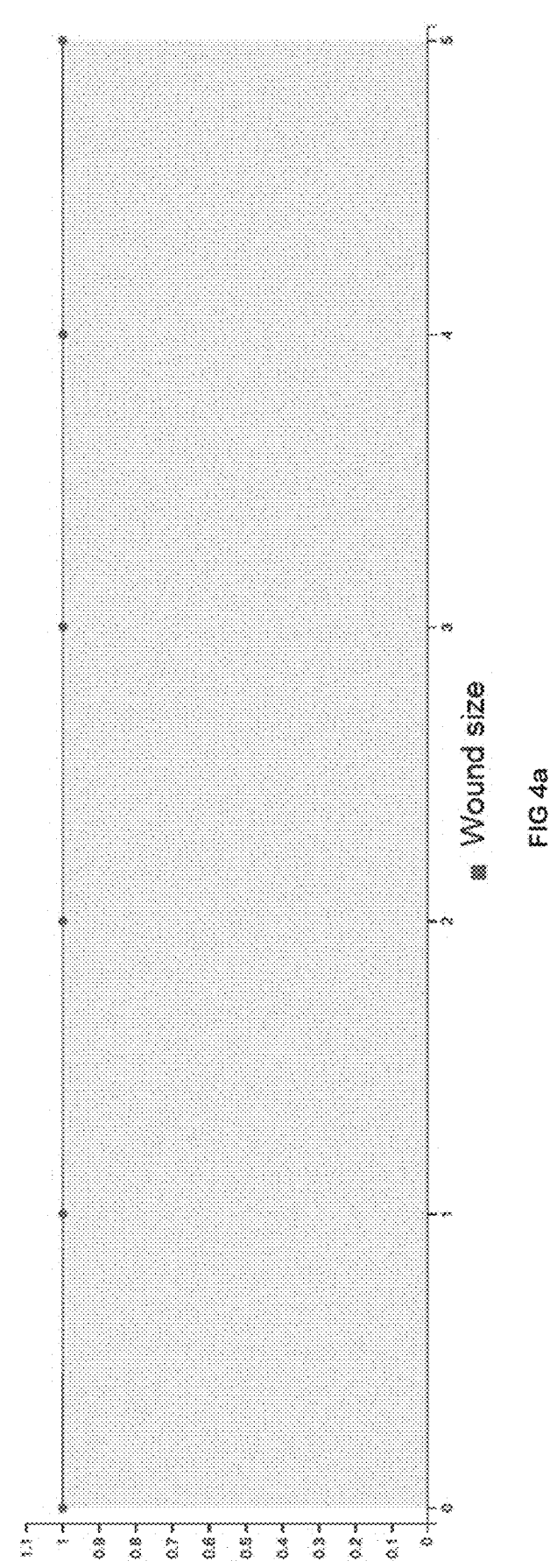
FIG. 4*a* shows the graphical representation of the characteristic values of an example scale that make up the patient's risk scale vector, showing the score of the scale enlarged.
Figure 4B:
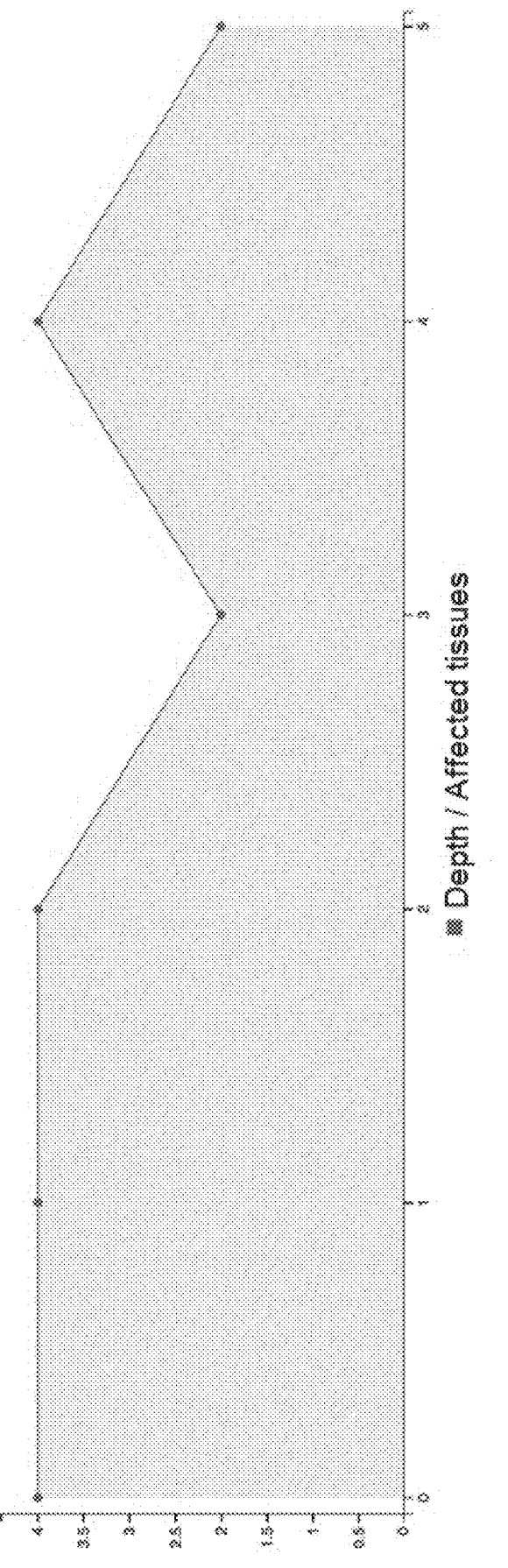
Figure 4C:
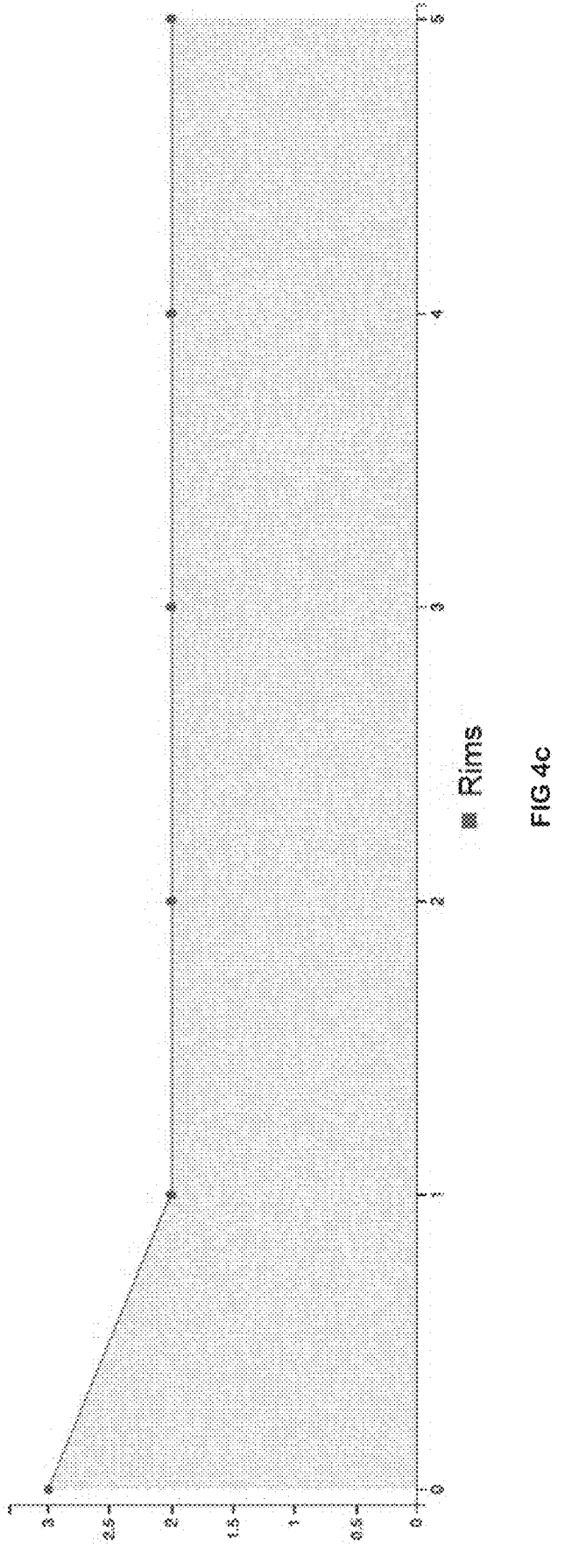
Figure 4D:
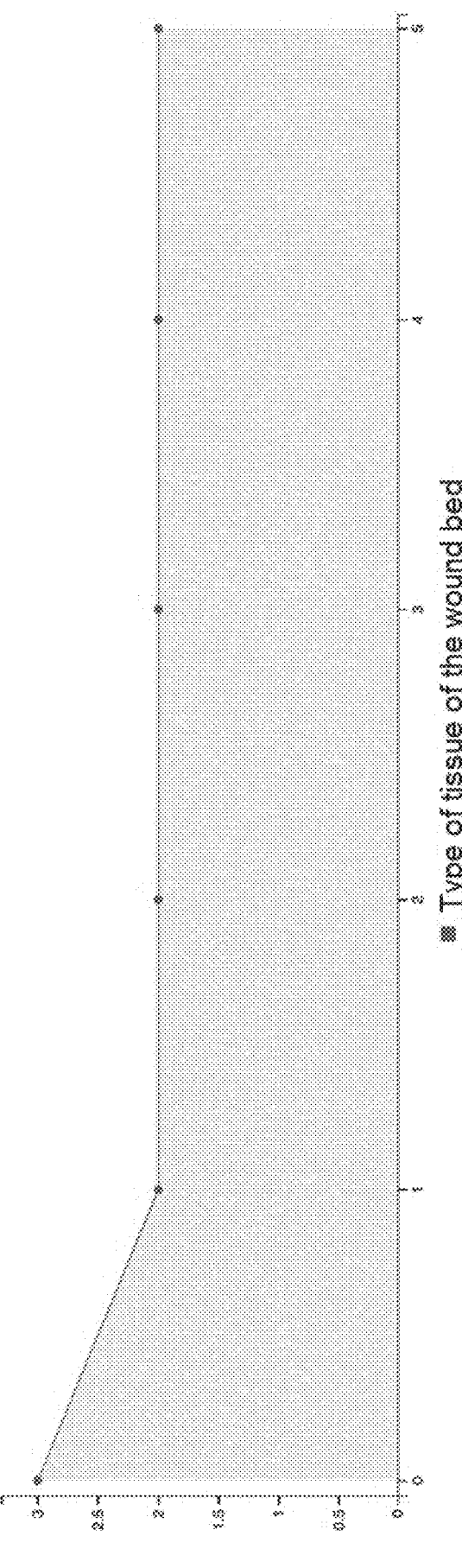
Figure 4E:
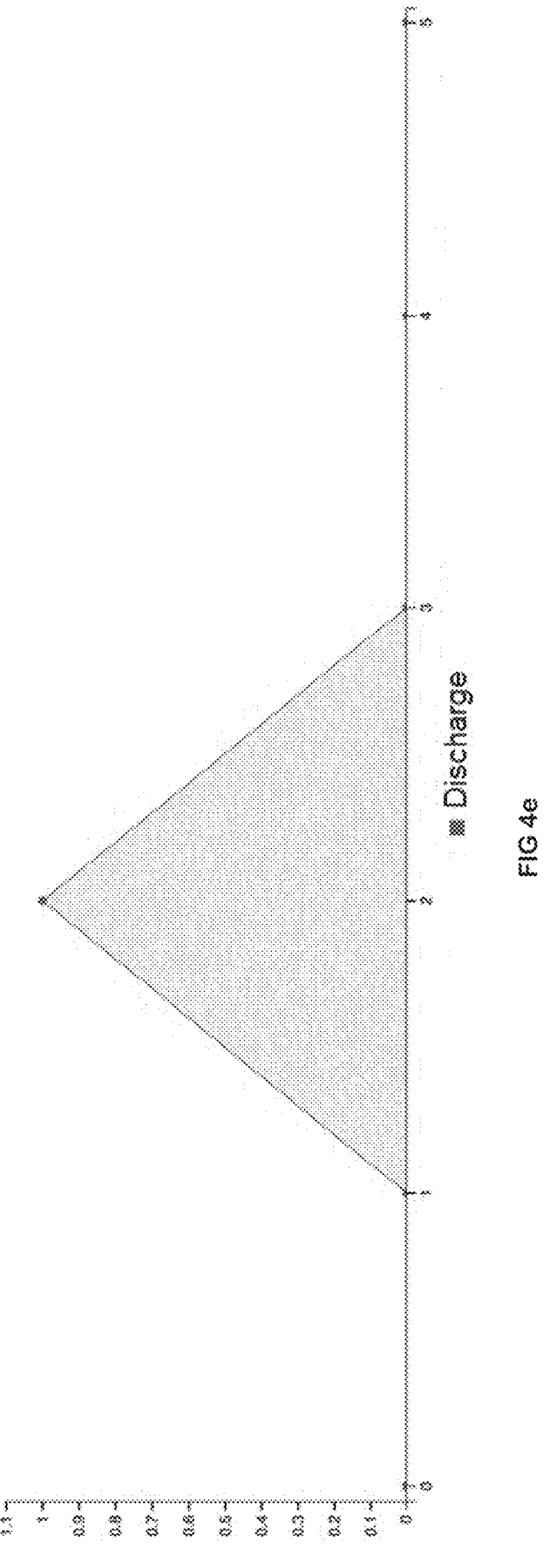
Figure 4F:
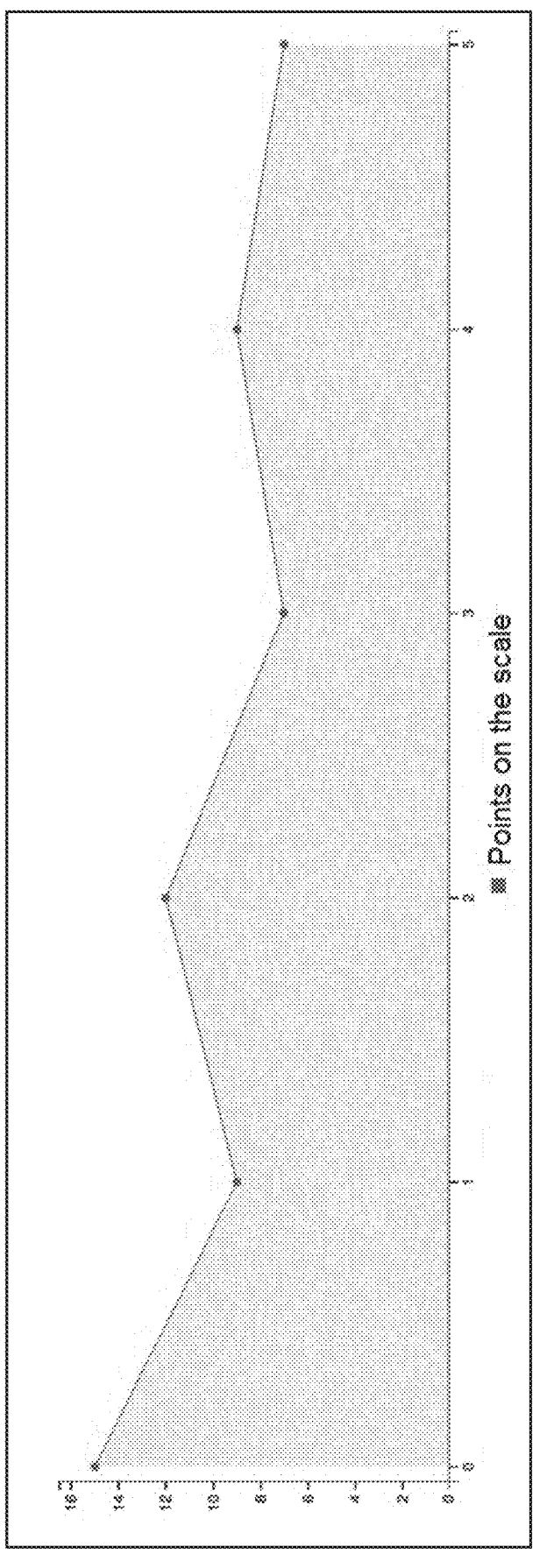

FIG. 4*b* shows the graphical representation of the characteristic values of an example scale that make up the patient's risk scale vector, showing the score of the scale enlarged;

FIG. 4*c* shows the graphical representation of the characteristic values of an example scale that make up the patient's risk scale vector, showing the score of the scale enlarged;

FIG. 4*d* shows the graphical representation of the characteristic values of an example scale that make up the patient's risk scale vector, showing the score of the scale enlarged;

FIG. 4*e* shows the graphical representation of the characteristic values of an example scale that make up the patient's risk scale vector, showing the score of the scale enlarged; and FIG. 4*f* shows the graphical representation of the characteristic values of an example scale that make up the patient's risk scale vector, showing the score of the scale enlarged.

DETAILED DESCRIPTION

The following references are indicated in these figures:
  1. Measurement of the ulcer area and ROI.
    1.*a*. Image of the ulcer area and ROI.
  2. Segmentation of tissues.
  3. Global characteristics vector.
  4. Global characteristics vector of the registered ulcer clinical data.
  5. Base characteristics vector.
  6. Patient data vector.
    6.*a*. Patient characteristics.
    6.*b*. Clinical data of the patient.
    6.*c*. Patient risk scale.

In relation to the figures and references listed above, an embodiment of the aspects of embodiments of the invention is illustrated, referring to an ulcer-related control, prognosis and comparative support procedure that comprises the following stages:

Measuring the area of the ulcer and ROI (1) by capturing an image of the area of the ulcer and ROI (1.*a*).

Segmenting the tissues (2) obtained in the image of the ulcer area and ROI (1.*a*).

Obtaining the base characteristics vector (5).

Depicting the state of the tissues.

Classifying ulcers.

Supporting decisions.

Archiving registered clinical cases.

As already mentioned, in this patent a vector or matrix is understood as a contiguous storage area that contains a series of elements of the same type, in our case, data. From the logical point of view, a matrix can be seen as a set of elements arranged in rows and columns and a vector as the set of matrix elements relating to a single row. The difference between vector and matrix lies in how these structures are accessed; while vectors are accessed with a subscript (indicating the position in the column), matrices use two subscripts (indicating the position in row and column).

The support to the decision of the user or specialist in embodiments of the present invention is carried out by the comparison of vectors; in particular, by comparing the global characteristics vector (3). In the global characteristics vector (3), the global data characterizing the specific clinical case being analyzed is stored. These data stored in the global characteristics vector (3) are compared with the global characteristics vectors of pre-existing registered ulcer clinical cases (4), the latter being the set of global characteristics vectors of previously analyzed, stored and registered ulcer clinical cases. In other words, each case analyzed using this procedure produces a global characteristics vector (3). Once stored, this vector becomes part of a "library" of vectors called global characteristics vectors of registered ulcer clinical cases (4). Each new global characteristics vector (3) is compared with each of the vectors that integrate the global characteristics vectors of the registered ulcer clinical cases (4). This comparison between vectors allows the data of the cases to be compared in a structured and objective way, making it possible to locate the clinical case whose characteristics are closest to the ulcer-related case that is being analyzed and support the specialist's decision, presenting the treatment and evolution of a case as similar as possible to the one being evaluated.

In application of this procedure, an example of execution would be the following.

Figure 1:
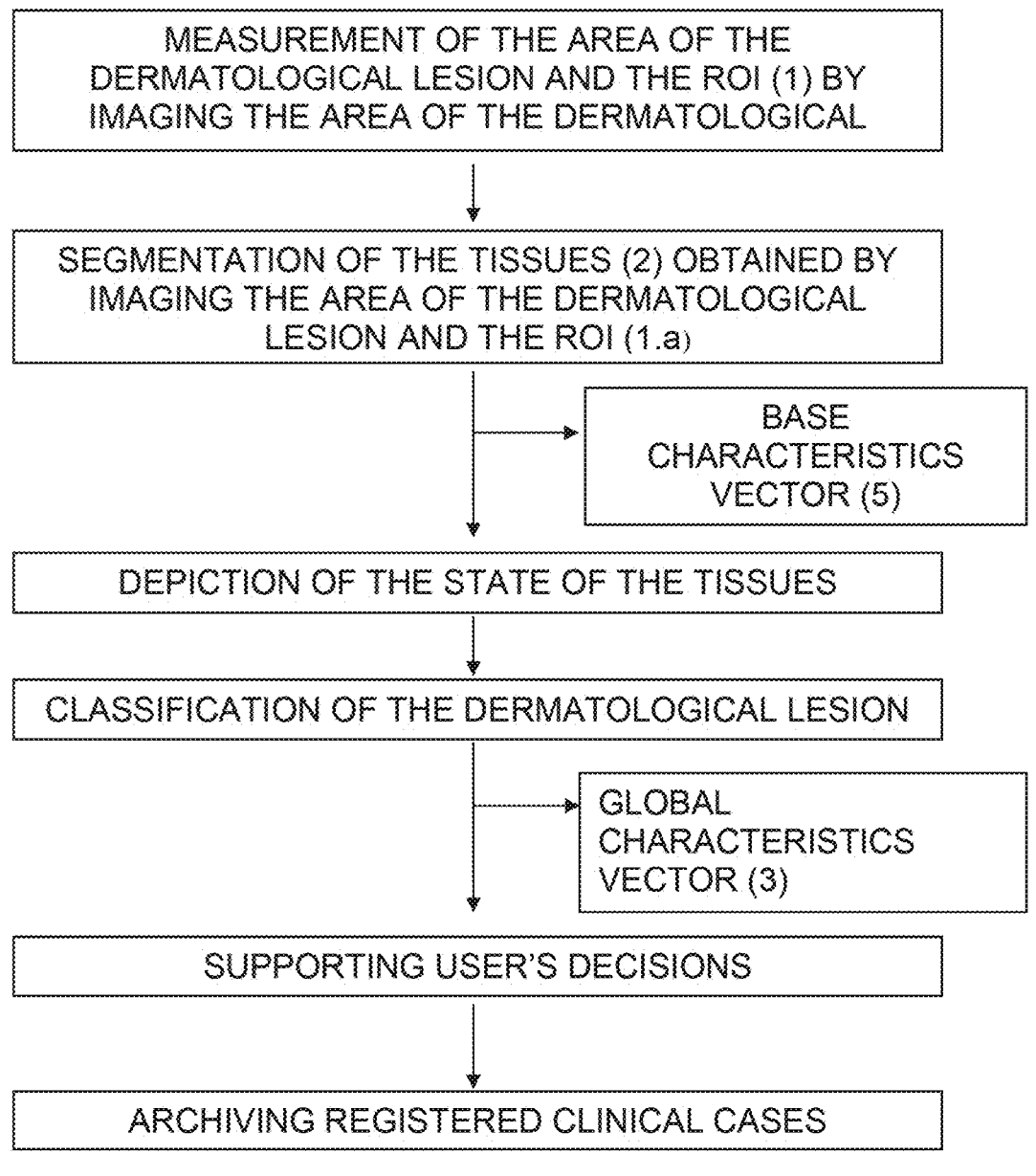
FIG. 1 shows a flowchart of the stages that make up the procedure.
Figure 2:
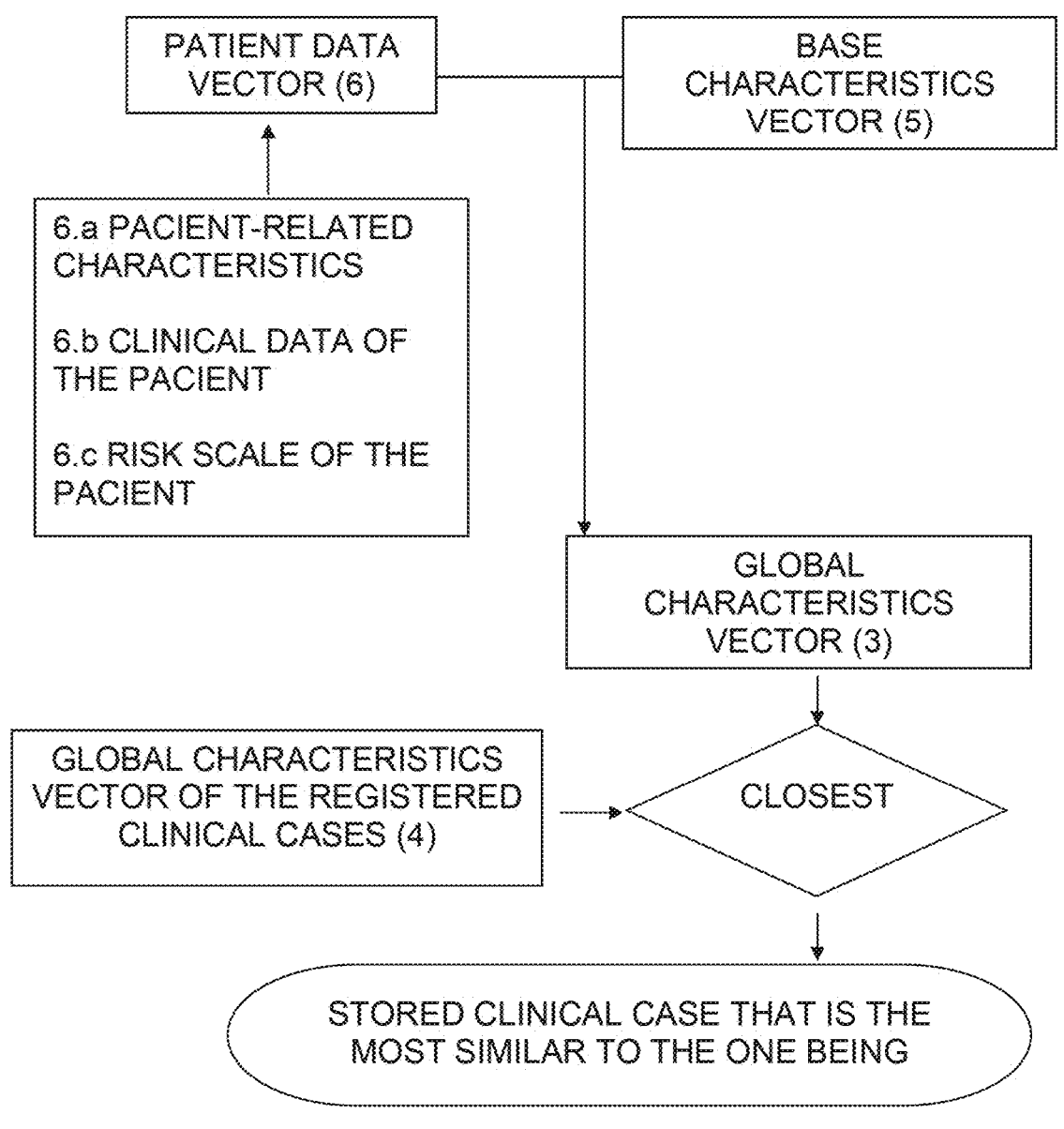
FIG. 2 shows a decision support flowchart.
Figure 3:
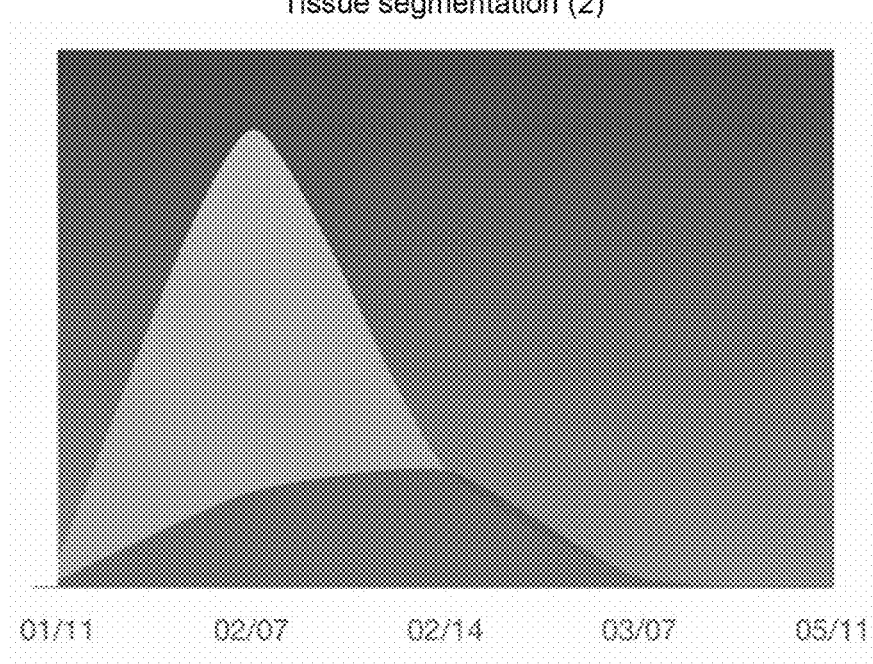
FIG. 3 shows the graphical representation of the segmentation of tissues and the evolution of the size of the ulcer that together form the base characteristics vector.
Figure 3:
Figure 3:
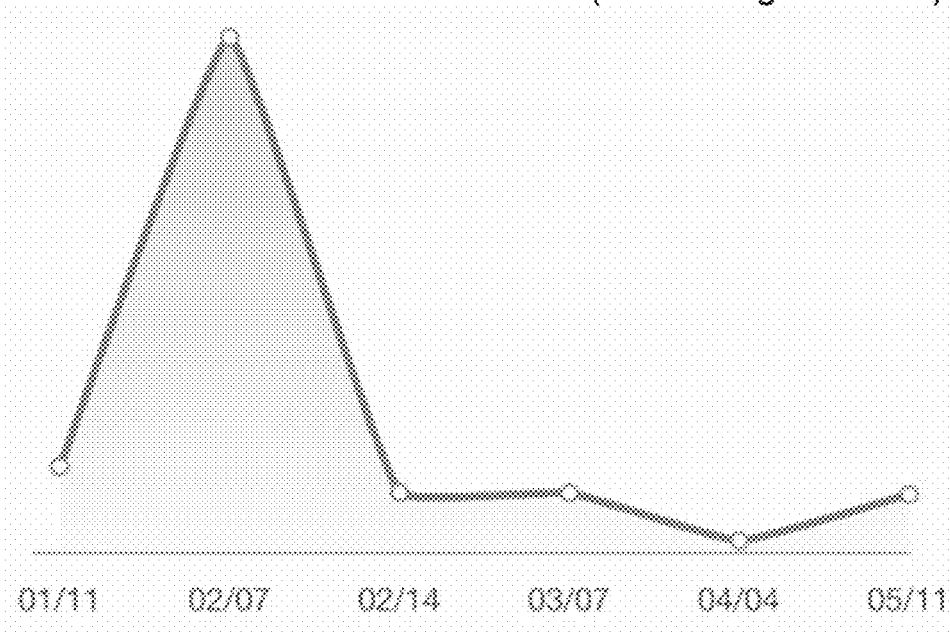

Taking as a reference a subject suffering from an ulcer located in the metatarsal area at the level of the fourth phalanx. To obtain the global characteristics vector (3), the different measurements taken at different visits are taken into account, starting from the image captured of the area of the ulcer and the region of interest (ROI) (1.*a*), which makes it possible to see the evolution of the ulcer as seen in FIG. 3. The tissues in the area of the ulcer are classified according to the type of tissue to which they belong (generally granulated, sloughy or necrotic), thus obtaining the segmentation of the tissues (2). With the data of the area of the ulcer and the type of tissues that it comprises, the base characteristics vector is obtained (5).

The patient's data vector (6) (the vector including the relevant patient- and file-related data for a better interpretation of the evolution of the ulcer area) is added to the base characteristics vector (5) thus obtained, to obtain a global characteristics vector (3) and this is compared with the global characteristics vectors of previous registered ulcer clinical cases (4) to obtain the registered clinical case whose characteristics most closely match the ulcer clinical case analyzed.

This comparison is mainly made by calculating the Euclidean distance between global characteristics vectors (the mathematical equation that allows a numerical value to be obtained that represents the shortest distance between two vectors). Thus, the distance between several registered global vectors (4) and the global characteristics vector (3) is calculated, the one with the lowest Euclidean distance being selecting, which will be the clinical case closest to the one analyzed. Therefore, we obtain the previous registered clinical case that most closely resembles the clinical case being analyzed. This procedure provides the user or specialist with data on the treatment used in the most similar registered ulcer clinical case and presents the results of this treatment to assist in decision-making.

As already mentioned, to improve the base characteristics vector (5), a patient data vector (6) is added thereto. This vector is formed from the characteristics data relating to the patient (6.*a*) (such as weight, height, age, etc.), in this example of execution;

Body Mass Index (BMI) of 25-29;

Palliative;

Non-smoker.

To which are added the patient's clinical data (6.*b*) (such as clinical analyses (diabetes, anemia, etc.), clinical tests (thermography, ultrasound, etc.), medical history (previous injuries, etc.). Thus, in an example of execution, this data would be:

Without coronary artery disease;

Without congestive heart failure;

With obstructive lung disease;

With diabetes;

No peripheral vascular disease;

With paraplegia;

No hypertension;

With a concurrent injury;

Wound characteristics: signs of biofilm

Perilesion erythema

Perilesion edema

Increase in temperature

Satellite lesions

Treatments received or medical history

Discharge

Polyurethane foam

Hydrogels

Nanocrystalline silver

Genomic incidence variants:

HIF-1$\alpha$

MCP-1-2518A/G

TLR9-1237 T/C

MAPK14 rs80028505

Just as the patient risk scale (6.*c*) is incorporated (scale data assigned by each center assessing each patient's risk, for example, Resvech) as observed in FIGS. 4*a*-4*e*.

When considering the comparison with previous cases, it is important for the user to base decision-making on cases where there is a similar evolution, in addition to a similar tissue composition. For this reason, the introduction of data that may influence the evolution of the ulcer (e.g., risk factors such as diabetes, heart problems, etc.) is considered an improvement in the comparison.

The introduction of the patient risk scale (6.*c*)—a risk vector determined by the center-makes it possible to standardize the use of the scale determined by the center, which is generally clinically validated, thereby reducing subjectivity in the evaluation of ulcers by the user.

The segmentation of the tissues obtained in the image of the ulcer area and ROI (1.*a*) and the obtaining of the vector of base characteristics (5) is carried out using the pre-trained CNNs (Convolutional Neural Networks). To do this, the CNN first segments the image (splitting the image into multiple parts). Afterwards, depending on its tissue type and based on the pre-training received, it classifies each image part as granulated, sloughy and necrotic, and hyper-granulated, as the case may be, then representing the classified tissues in the image, maintaining the classification in each image part. Thus, image areas with similar tissue characteristics that are indicative of the healing status of the ulcer are generated.

The tissue representation reconstructs the image based on the base characteristics vector (5), representing each type of tissue with a specific color (usually red for granules, yellow for slough and black for necrotic). Thus, the image taken of the area of the ulcer and of the ROI (1.*a*) is obtained with the fractions highlighted in one color or another depending on the type of tissue that it comprises (visually, with areas highlighted in different colors), thereby facilitating the interpretation of the ulcer at a glance. Thus, the user can quickly check the ulcer's evolution by viewing the tissue composition highlighted in colors familiar to the user on the image itself, automatically identifying a tissue type.

The measurement of the ulcer's area and ROI (1) by imaging is carried out with the image captured of the ulcer area and the region of interest (ROI) (1.*a*) processed using an API (Application Programming Interface). The image may be a conventional image, or a thermographic image, or any imaging mode that can be technologically developed. The API allows the distance in cm between two points of an image to be obtained. Using the data provided by the API, the area of the ulcer in cm² is determined. This data allows the user to better monitor the evolution of the ulcer without the need to use invasive methods that require direct contact with the ulcer and the consequent disorders that the patient may experience.

The procedure is based on an image that can be acquired with any mobile device such as a phone or tablet, or any type of device that can be connected to the internet and is capable of taking a photograph. Therefore, the patient should not move, and this procedure can be applied in home care or telecare.

In the case of thermographic images, a conventional thermal camera should be attached to the mobile device. For this type of image, it would be necessary to use a certain biocompatible adhesive caliper, which would be placed at the same level as the wound, always applied without direct contact with the ulcer. It is a specific adhesive because the temperature that it radiates is clearly distinguishable from that which the skin of the ulcer in question can radiate.

This procedure analyses not only the area of the ulcer, but also the area of the ulcer and the ROI, which allows the surrounding area and its evolution over time to be observed. This is how the tissue surrounding the area of the ulcer is checked, which, despite not being part of the ulcer at first, may be affected by it depending on its evolution and become part of the clinical case file.

Although the present invention has been disclosed in the form of embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The invention claimed is:

1. An ulcer-related control, prognosis and comparative support procedure comprising:
   measuring an area of an ulcer and ROI by taking an image of the area of the ulcer and ROI;
   segmenting tissues obtained in the image of the ulcer area and ROI;
   obtaining a base characteristics vector;
   depicting a state of the tissues;
   classifying the ulcer;
   supporting a user's decisions;
   archiving registered clinical cases,
wherein the user's decisions are supported by comparing a global characteristics vector related to the ulcer with a global characteristics vectors of registered ulcer clinical cases;
wherein the global characteristics vector is obtained by obtaining the base characteristics vector of the segmentation of the tissues of the image of the area of the ulcer and ROI and adding patient data vector, wherein the patient data vector is obtained from patient-related characteristics, clinical data of the patient and patient risk scale;
wherein the global characteristics vector is compared with the global characteristics vectors of registered ulcer clinical cases to obtain a closest registered clinical case with characteristics closest to those of the ulcer-related analyzed clinical case, wherein the closest registered clinical case has the lowest Euclidean distance; and
wherein the measurement of the area of the ulcer and ROI by taking images is carried out with the image taken of the area of the ulcer and the region of interest (ROI) processed by an API using distance in cm between two points on the image as a reference for determining the area of the ulcer and ROI in cm².

2. The ulcer-related control, prognosis and comparative support procedure according to claim 1, wherein the segmentation of the tissues obtained in the image of the area of the ulcer and ROI and the obtaining of the base characteristics vector is performed using the pretrained CNNs (Convolutional Neural Networks), which classify tissues as granulated, sloughed, necrotic, and hyper-granulated.

3. The ulcer-related control, prognosis and comparative support procedure according to claim 1, wherein the representation of the tissues reconstructs the image based on the base characteristics vector representing each type of tissue with a specific color.

4. The ulcer-related control, prognosis and comparative support procedure according to claim 1, wherein the global characteristics vector of the ulcer clinical case is archived in a safe environment.

* * * * *